(12) United States Patent
Graham

(10) Patent No.: US 6,905,334 B2
(45) Date of Patent: Jun. 14, 2005

(54) ATTACHMENT OFFSET TOOTH EYELET

(76) Inventor: Neil John Graham, 6017 Lido La., Long Beach, CA (US) 90803

(*) Notice: Subject to any disclaimer, the term of this patent is extended or adjusted under 35 U.S.C. 154(b) by 28 days.

(21) Appl. No.: 10/389,590

(22) Filed: Mar. 17, 2003

(65) Prior Publication Data

US 2004/0185411 A1 Sep. 23, 2004

(51) Int. Cl.[7] ................................................ A61C 7/00
(52) U.S. Cl. .......................................... 433/21; 433/18
(58) Field of Search .............................. 433/21, 22, 18, 433/15, 9, 8

(56) References Cited

U.S. PATENT DOCUMENTS

| 3,835,538 A | * | 9/1974 | Northcutt | 433/9 |
| 5,078,597 A | * | 1/1992 | Caplin | 433/18 |
| 2003/0049583 A1 | * | 3/2003 | Pitnick et al. | 433/18 |

* cited by examiner

Primary Examiner—Melba Bumgorner
(74) Attorney, Agent, or Firm—Neil John Graham

(57) ABSTRACT

The invention is an orthodontic bondable offset tooth eyelet which is attached to the lingual surface of an impacted tooth placing an orthodontic force attaching eyelet on an unattachable labial or buccal surface, the labial placement assures the tooth will arrive in its final position rotationally correct.

6 Claims, 4 Drawing Sheets

ATTACHMENT OFFSET TOOTH EYELET

FIELD OF INVENTION

The present invention is directed to an offset eyelet mechanism attachable to an impacted tooth during orthodontic procedures, the configuration of the eyelet allows the orthodontic pressure to be exerted to the center of the labial surface of an impacted tooth.

BACKGROUND OF THE INVENTION

The orthodontic procedure today for aligning an impacted tooth involves attaching, usually by bonding, a mesh backed metal pad with an eyelet to a surgically uncovered tooth. The patient is usually in a full orthodontic appliance to which an attachment is made to the labial eyelet of the impacted tooth. The attachment to the eyelet is a force which will move the impacted tooth towards the orthodontic appliance and into its aligned position. Often the only accessible surface of the impacted tooth for attaching the eyelet to is the lingual surface of the impacted tooth. This is especially true for palatally impacted maxillary cuspids. It is desirable to attach the orthodontic pressure to the labial surface of the impacted tooth. When orthodontic movement pressure is exerted to this part of the tooth the lingual surface of the tooth is moved towards the labial of the patients mouth. Once the tooth is in position it often has to be rotated 180 degrees which is time consuming and lengthens the patient's time in orthodontic appliances. When the orthodontic pressure is applied from the appliance to the center of the labial surface of the tooth the tooth is drawn towards the orthodontic appliance first and the tooth ends up in its correct rotational position.

SUMMARY OF THE INVENTION

In order to better understand the invention dental terminology should be explained. An orthodontic appliance consists of a series of orthodontic brackets attached to the patient's teeth. The following dental terminology is used: buccal or labial is towards the patient's cheek; lingual is towards the tongue; gingival is towards the gums; anterior is towards a front of the mouth; posterior is towards the back of the mouth; incisors are the front teeth; molars and bicuspids are the back teeth; maxilla is the upper jaw; mandible is the lower jaw; occlusal is the chewing area of the teeth; mesial is towards the midline of the mouth and distal is away from the midline of the mouth; and intermaxillary is between the jaws.

The present invention is directed towards an attachable offset tooth eyelet which can be bonded to the lingual surface of a tooth. The attachable offset tooth eyelet comprises a planar sheet of stainless steel metal of sufficient dimension to fit within the lingual crown surface of a patient's tooth. One surface of the stainless steel sheet has a stainless steel mesh pad attached to it allowing this surface to be bonded to the surface of the tooth. The second surface of the stainless steel sheet has a configured wire attached to it approximately 0.025 in. in diameter. The configured wire, at its beginning, has a first longitudinal leg which extends at least 2 mm. and parallel to the second surface of the metal sheet. The wire in its longitudinal axis turns occlusally, or at a right angle to the sheet of metal, and forms a 2 mm. diameter circle which facilitates the gripping of the tooth eyelet by a dental instrument during the fitting and placement of the attachable offset tooth eyelet. The wire then returns to the same longitudinal axis as the first leg and extends axially away from the first leg to form a second leg. The first and second legs are welded, soldered, or adhesively attached to the second surface of the pad. The wire then continues approximately 4 mm. on the same axial plane and direction as the first and second legs where an arcuate bend extends in the general direction of the mesh surface of the pad. The direction of the wire is approximately 45 degrees to its original direction, the arcuate bend passing over the tooth incisal edge onto the labial surface of the tooth. The wire then extends at least 2 mm. and turns back on itself to form an eyelet at least 2 mm. in diameter. The eyelet is the attachment point of the orthodontic force which will move the tooth into position. The positioning of the eyelet on the labial of the tooth assures the tooth will be in its correct rotational position when it is moved into its correct axial position.

In an alternative of the present invention, the attachable offset tooth eyelet comprises a configured wire with a handle for positioning the configured wire during fitting to the patient's tooth. The configured wire at its one end has an eyelet formed to lay parallel to the lingual surface of the tooth crown. This parallel eyelet is bonded to the patient's tooth. The wire is then configured similar to the mesh eyelet where it is bent to adapt over the incisal edge of the tooth and ends with an offset force attaching eyelet positioned in the center of the labial surface of the patients tooth. The wire continues from the offset force attaching eyelet longitudinally in a plane that approximates the patient's occlusal plane when the eyelet is placed in the patient's mouth. The direction of the longitudinal wire is towards the left side of the patients mouth allowing the appliance to be held by the left hand during the fitting in the patient's mouth, leaving the right hand free to adjust the attachable offset tooth eyelet appliance. The handle is of sufficient length it extends beyond the patient's mouth, approximately 40 mm. in length. The handle portion at its end is configured in a planar 10–20 mm. square facilitating the hand holding of the eyelet appliance in a repeatedly similar position relative the tooth it is being fitted to.

In another embodiment of the wire configured attachable offset tooth eyelet appliance the wire may be configured to reach the labial surface of the tooth from the lingual surface by circling the mesial or distal surface of the tooth.

The configured wire in its most common embodiment is configured to fit a palatally impacted cuspid, which is the most common impaction.

In another embodiment of the eyelet appliance all wire is used configured to resemble the mesh pad combination. Instead of the mesh pad, the wire is configured in an eyelet parallel to the lingual surface of the patients tooth. The configured wire has a vertical 2 mm. diameter eyelet occlusal to the parallel eyelet which facilitates holding the eyelet during its fitting and final placement in the patient's mouth.

DETAILED DESCRIPTION OF THE INVENTION

Figure 1:
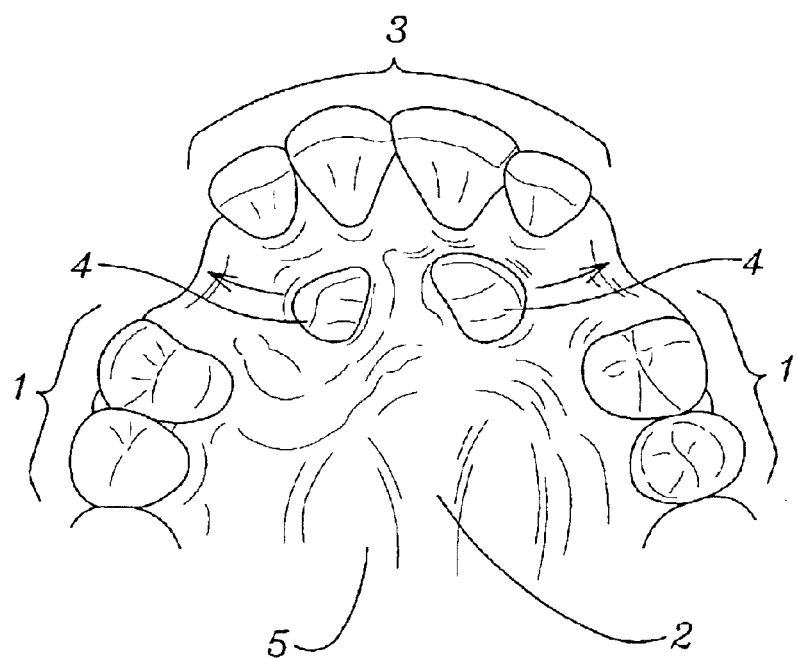
FIG. 1 is an occlusal view of a patient's upper palate.
Figure 2:
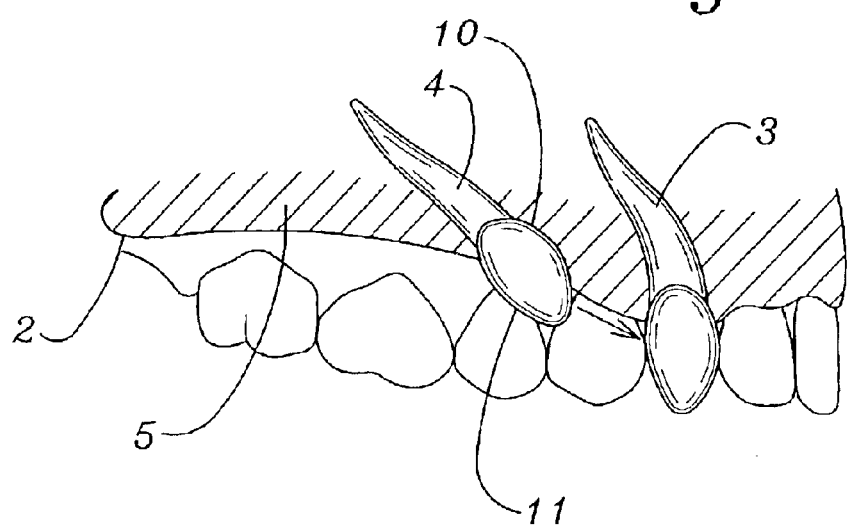
FIG. 2 is a side view of a patient's upper teeth.
Figure 3:
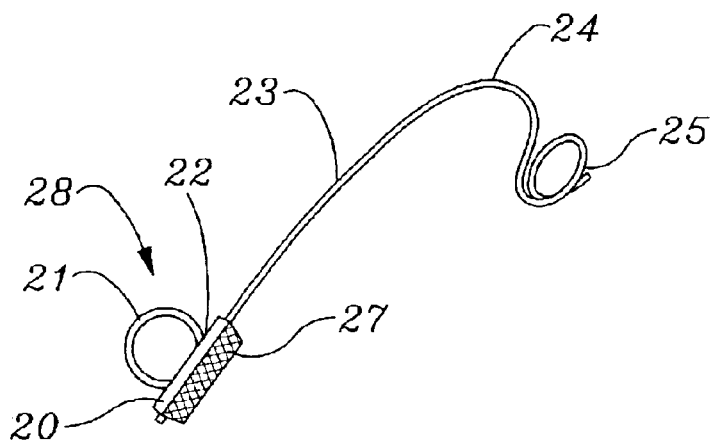
FIG. 3 is a view of the offset tooth eyelet.
Figure 4:
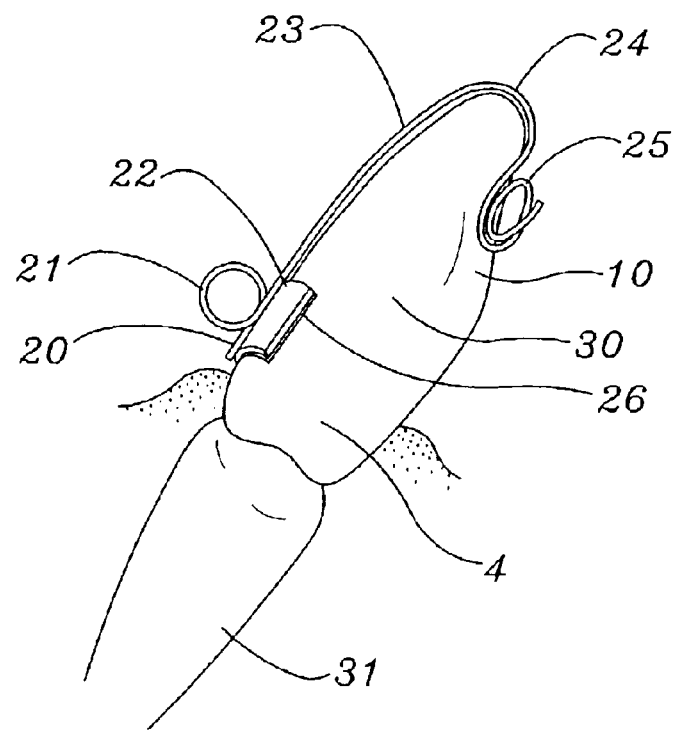
FIG. 4 is a view of the offset tooth eyelet positioned on a tooth.

Referring to FIGS. 3 and 4, the attachable offset tooth eyelet has a stainless steel pad 26 with the mesh backing 27 for adhesion to a tooth 30 as in FIG. 4. Soldered or electro-welded to the occlusal surface of a stainless steel pad 26 is a wire member 28 of the attachable offset tooth eyelet comprised of 0.014–0.025 inch diameter stainless steel. The preferred embodiment is 0.020 inch diameter wire. The wire member 28 has a horizontal first leg 20 which is parallel to the metal pad 26. The horizontal first leg 20 is 2–4 mm in length and has the same axial direction as the lingual tooth surface 4 when the attachable offset tooth eyelet is positioned on the lingual surface of the tooth 4. The wire then turns at a right angle away from the tooth surface and forms an occlusal vertical eyelet 21 2–3 mm in diameter. The planar dimension of the vertical eyelet 21 is the same direction as the axial direction of the first leg 20. The wire continues from the vertical eyelet 21 and forms a second leg 22 in the same plane and axial direction as the first leg 20. The second leg is 2–4 mm in length. The first leg 20 and the second leg 22 are soldered or electro-welded to the occlusal surface of the metal pad 26. A horizontal extension 23, as shown in FIGS. 3 and 4, extends in the same plane and axis as the first leg 20 and the second leg 22 2–4 mm where it forms an arcuate curve 24 which passes over the incisal edge of the crown of the tooth to the lingual surface 11 of the tooth. The wire then travels 2–4 mm in the axial direction of crown of the tooth. This distance is often limited for impacted maxillary cuspids as shown in FIGS. 1 and 2. The labial surface 10 of the cuspids are often under the gums and away from view which limits the distance the wire can travel on the labial surface of the tooth as shown in FIG. 2. In FIGS. 3 and 4 the wire is then formed back approximately 160 degrees on itself into a labial eyelet 25, the plane of which is approximately parallel to labial surface 10 of the tooth. A pulling orthodontic force is applied to the labial eyelet 25, moving the impacted tooth into the dental arch where it belongs, as shown 3 in FIG. 1. By applying the force to the labial eyelet 25 on the labial of the tooth, the tooth will arrive into its correct rotational position.

Figure 5:
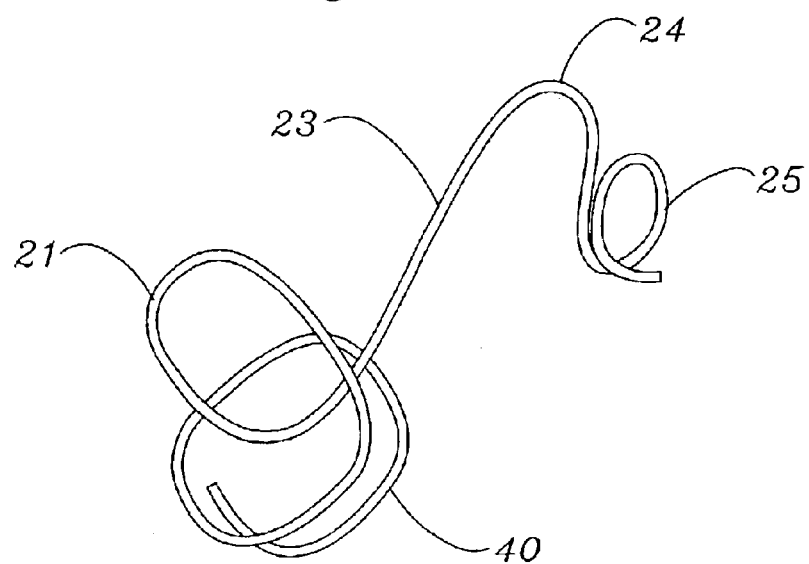
FIG. 5 is a view of the offset tooth eyelet with a configured wire bonding base.

The attachable offset eyelet shown in FIG. 5 is very similar to the one shown in FIGS. 3 and 4, with the exception the mesh pad 26 is replaced with a wire base 40 formed from the continuation of the first leg 20. The wire base 40 is configured as a circle 2–4 mm in diameter in the same plane the mesh pad 27 was. The wire continues to form the vertical eyelet 21 which allows the offset eyelet to be gripped by an instrument in its fitting and placement.

Figure 6:
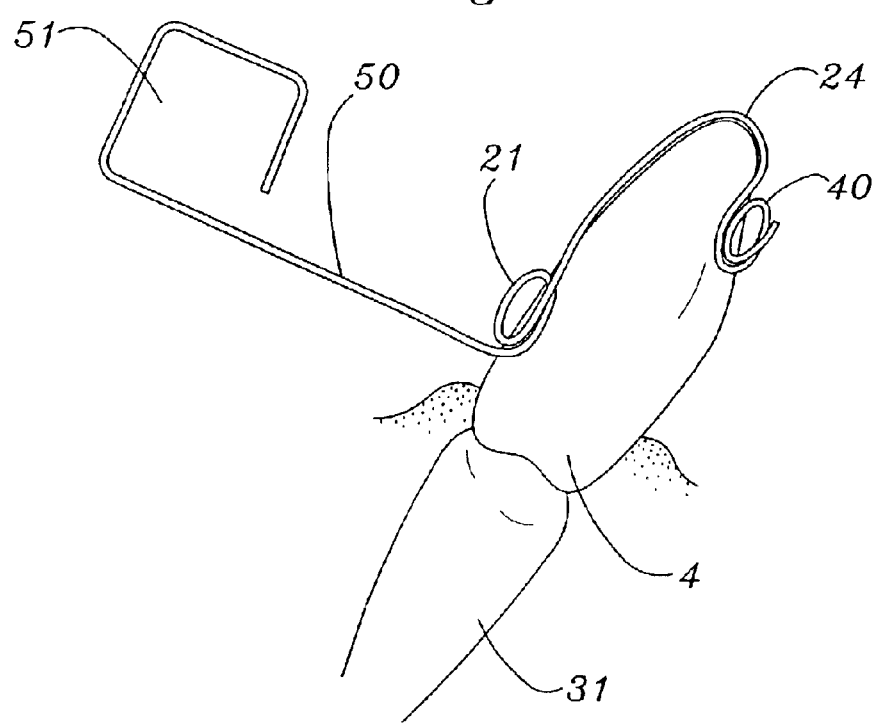
FIG. 6 is a view of the offset tooth eyelet with a positioning arm and handle.

In another embodiment in FIG. 6 a positioning extension 50 with a handle 51 is attached to the offset eyelet facilitating ease of fitting and placing the attachable offset tooth eyelet. In FIG. 6 a handle 51 is shown attached to a wire base. Another embodiment is to attach the positioning handle to the labial eyelet 25. FIG. 1 shows an upper jaw, or maxilla, from an occlusal direction. The posterior teeth 1 and anterior teeth 3 are shown. Impacted cuspids are shown in the palatal 5 area. Impacted cuspids 4 are shown in a common position in the palate 2. When the offset eyelet is fitted to either cuspid 4 the positioning handle would extend longitudinally towards the left a sufficient distance to leave the mouth area, probably 40 or 50 mm. In FIG. 6 the positioning handle 50 end is formed into a 10 mm by 10 mm planar handle end 51 to form an area to hold the offset tooth eyelet in a stable manner that allows the offset tooth eyelet to be repeatedly placed in the patient's mouth in the same relative position.

Figure 7:
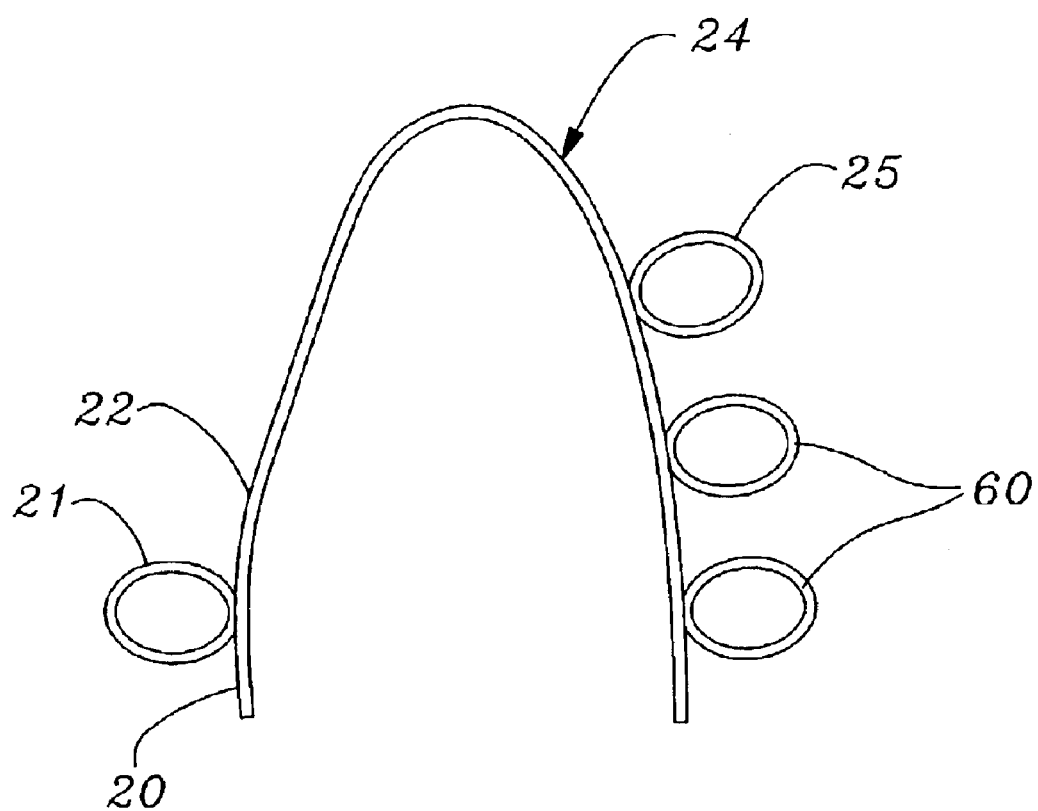
FIG. 7 is a view of the offset tooth eyelet with multiple attachment eyelets.

In FIG. 7 multiple labial eyelets 25 and 60 are shown. Depending upon the amount of labial surgical exposure the additional eyelets 60 would extend the point of orthodontic pressure axially to the center of crown 30 of the labial 10 of the tooth as shown in FIG. 4. This multiple eyelet design 25 and 60 allows one design to be constructed for all situations where an unwanted labial eyelet 60 can be clipped off during the fitting. Single labial eyelet 25 embodiments can be used with sizes placing the labial eyelet 25 at different levels down the labial surface 10 of the tooth.

The invention has been discussed with specific embodiments. However, the intent of the invention is to provide an the labial of an impacted tooth in a situation where the eyelet cannot be directly to the labial surface of the tooth. The object of the invention is to facilitate moving an impacted tooth into its correct rotational by applying the orthodontic force directly to the labial surface of the impacted tooth.

What is claimed is:

1. An attachable offset tooth eyelet for attaching a force to an impacted tooth during orthodontic treatment comprising:

a longitudinal wire having first and second ends, a top and bottom and a longitudinal axis, the longitudinal wire of sufficient length that it may be adaptably fitted to the lingual surface of a tooth;

an arcuate curvature wire with first and second ends, the first end continuous with the longitudinal wire second end wherein the curvature is sufficient that the arcuate curvature wire is contoured so that it may be adaptably fitted to the incisal edge of the tooth and the curvature wire second end is flat so that it may be adaptably fitted to the labial surface of the tooth;

a labial eyelet formed in a loop attached and continuous with the second end of the arcuate curvature wire wherein the loop is planar, the loop's plane forming an acute angle with the second end of the arcuate curvature wire, so that it may be adaptably fitted to the center of the labial surface of the tooth; and a means for attaching the longitudinal wire to the tooth comprising a metal pad with a top and a bottom, the bottom of the mesh pad having a mesh surface wherein the bottom of the longitudinal wire is soldered or electro-welded to the top of the pad and the mesh surface is adapted to be bonded to the lingual surface of the impacted tooth.

2. The attachable offset tooth eyelet as in claim 1 wherein a planar extension 2–4 mm in diameter projects at a right angle upwards from the top of the metal pad to allow gripping of the attachable offset tooth eyelet during its fitting and placement.

3. The attachable offset tooth eyelet as in claim 1 wherein the longitudinal wire, arcuate wire, and offset labial eyelet are integral and formed from stainless steel wire.

4. The attachable offset tooth eyelet as in claim 1 wherein the metal pad and mesh are stainless steel.

5. The attachable offset tooth eyelet as in claim 1 wherein the attachable offset tooth eyelet is comprised of 0.016–0.025 inch diameter wire.

6. The attachable offset tooth eyelet as in claim 1 wherein the attachable offset tooth eyelet is comprised of 0.020 inch diameter wire.

* * * * *